(12) United States Patent
Shapiro et al.

(10) Patent No.: US 7,988,657 B2
(45) Date of Patent: Aug. 2, 2011

(54) BODY CAVITY IRRIGATION DEVICE

(75) Inventors: Mishail Alexander Shapiro, Long Grove, IL (US); Aleksey Pirkhalo, Chicago, IL (US); Leonid Khodor, Orange, OH (US)

(73) Assignee: Inspector Medical, LLC, Long Grove, IL (US)

( * ) Notice: Subject to any disclaimer, the term of this patent is extended or adjusted under 35 U.S.C. 154(b) by 142 days.

(21) Appl. No.: 12/175,222

(22) Filed: Jul. 17, 2008

(65) Prior Publication Data

US 2010/0016787 A1 Jan. 21, 2010

(51) Int. Cl.
*A61M 1/00* (2006.01)
*A61M 5/178* (2006.01)

(52) U.S. Cl. ................ 604/27; 604/30; 604/36

(58) Field of Classification Search ........ 604/27, 604/275–279, 152, 184, 30, 31, 34, 35, 36; 118/300

See application file for complete search history.

(56) References Cited

U.S. PATENT DOCUMENTS

| | | | | |
|---|---|---|---|---|
| 4,180,722 A | * | 12/1979 | Clewans | 219/502 |
| 5,030,202 A | * | 7/1991 | Harris | 604/27 |
| 5,364,343 A | * | 11/1994 | Apolet et al. | 604/43 |
| 5,685,851 A | | 11/1997 | Murphy et al. | |
| 5,735,833 A | * | 4/1998 | Olson | 604/289 |
| 5,833,675 A | * | 11/1998 | Garcia | 604/310 |
| 6,210,358 B1 | | 4/2001 | Roger | |
| 6,458,094 B1 | * | 10/2002 | McMahon et al. | 604/35 |
| 6,485,451 B1 | | 11/2002 | Roberts et al. | |
| 6,706,023 B1 | | 3/2004 | Huttner et al. | |
| 6,949,088 B2 | | 9/2005 | Macrae | |
| 2008/0214891 A1 | * | 9/2008 | Slenker et al. | 600/109 |
| 2010/0262073 A1 | * | 10/2010 | Henniges et al. | 604/82 |

* cited by examiner

*Primary Examiner* — Theodore Stigell
*Assistant Examiner* — Imani Hayman
(74) *Attorney, Agent, or Firm* — Leonid Khodor

(57) ABSTRACT

A hand-held disposable body cavity irrigation device comprises a pump with an inlet and an outlet, a container for lavage fluid fastened removably to said pump, an applicator having an insertion tip, and divided longitudinally into an injection chamber with a first fitting and a drain chamber with a second fitting, and a first tube connecting said outlet to the first fitting wherein the first tube comprises at least one malleable element embedded longitudinally into an elastic wall, said inlet communicates with the lavage fluid within the container, and the drain chamber is disposed predominantly below the injection chamber and has at least one vent beyond the insertion tip.

2 Claims, 4 Drawing Sheets

BODY CAVITY IRRIGATION DEVICE

BACKGROUND OF THE INVENTION

The present invention relates to devices for injecting liquid into a body cavity to effect cleaning thereof and, more particularly, a device for irrigation of an external ear canal with lavage fluid.

Various irrigation devices are known for cleaning human body cavities. For example, such devices are used routinely for cleaning the ears of a patient. Most commonly, a flexible bulb is fitted to a nozzle through which the lavage fluid is discharged into the ear canal of a patient.

Bulb-type devices have several drawbacks. First, the bulb capacity limits the usage of the device since the bulb contains a relatively small quantity of the lavage fluid and, to fully irrigate a patient's ear, the bulb has to be refilled a number of times.

Second, the pressure of the lavage fluid exiting the nozzle and impinging upon the ear canal can not be readily controlled in a reliable manner. This lack of control produces inconsistent results and can in turn, cause pain and injure a patient due to the sensitivity of the tympanic membrane.

Third, an inconvenience related to collection of the waste fluid discharged from the cavity. In the majority of prior art devices a basin is used to collect the waste fluid. If the basin is not used, then the patient must be irrigated in the vicinity of a sink in order to avoid spillages and further usually require the use of towels, drapes, and other accessories to attend to the discharged lavage fluid. Using either method, the collection of waste fluid from a cleaning procedure is tedious and messy, as well as inefficient.

There is known an ear irrigator which delivers a stream of water into an ear canal, body cavity or wound in small volume bursts of short duration. The device comprises a bottle containing a volume of water and attached to a hand-held pump actuated by squeezing the trigger, a flexible tube with a splash shield connected to the outlet of the pump, and an end tube connected to the free end of the main conduit tube, the end tube being of reduced outer and inner diameter relative to the flexible tube. The transition from a relatively large internal bore in the flexible tube to a small internal bore in the end tube creates a high velocity flow at the tip and causes the end tube to oscillate during the delivery of the water stream that creates a pulsing water stream relative to any particular location in the ear canal and may be more effective in removing ear wax and debris than a steady stream of water. Although the device is an improvement in terms of the liquid capacity, it does not address the other inadequacies of the bulb-type devices.

Another known irrigation devices include a pump, connected to a fluid reservoir, and driven by an electric motor. Such devices are capable of pulsatingly or continuously ejecting water from a nozzle opening for a sustained period of time, but do not generally include temperature and pressure indicators for monitoring the temperature and pressure of the water issuing from the nozzle. The use of an electric motor also has a number of inherent disadvantages, including a necessarily maintenance of the device and the noise of the motor, which can be annoying and stressful both for the operator and the person whose ear is being cleaned.

Fountain-type irrigation devices which are adapted to be connected with a pressure water supply such as at a faucet, on top of having some of the disadvantages of the pump devices, are generally suited for cleaning ears with water only, feature long tubes that necessitate prolonged flashing for stabilizing of the water temperature and inconvenient for the operator, and require pressure relief valves with a separate drain line for dampening of water supply pressure fluctuations. Moreover, the rapid opening and closing of the relief valve can itself create a pulsating flow from the nozzle opening.

A common problem of using the irrigation devices with continuous supply of the lavage fluid is the waste fluid evacuation. Due to the continuous flow, a protection of patient clothes and the collection of waste fluid from a cleaning procedure are more challenging than with the manual devices. Known in the fountain-type irrigation devices, a vacuum assisted evacuation can work effectively only under certain conditions, which are not sustainable in real settings.

Another problem long encountered in the field pertains to the temperature of lavage fluid being discharged into the body cavity, especially in those systems that utilize a continuous lavage fluid supply. Lavage fluid which is too hot can create discomfort and in other cases could seriously injure the patient. It has further been determined that lavage fluid which is too cold will not allow optimal cerumen removal. It has been determined that optimal removal is achieved using lavage fluid which is at approximately body temperature.

Each of the known devices is intended to remove cerumen which has accumulated in the external ear canal. However, each of the known devices involves the possibility of damaging the tympanic membrane, the necessity of professional care, or both. However, with each visit to a doctor, costs are incurred. As well, the time spent by patients in attending at doctors' offices to have cerumen removed is cumulatively significant.

Therefore it would be desirable to provide an inexpensive, ready and easy to use a body cavity irrigation device capable of holding sufficient volume of lavage fluid, discharging the lavage fluid at a safe and effective pressure, and evacuating reliably waste fluid directly from the cavity. Additionally, it would be desirable if such device included a temperature indicator, which could be used for adjusting and monitoring the temperature of the lavage fluid at the time of use. Further, such device should preferably be safe and convenient for users to self administer the cavity irrigation with no professional supervision.

SUMMARY OF THE INVENTION

The present invention generally focuses on improved body cavity irrigation device in general and ear irrigation device specifically that is equally safe, easy and convenient to use by medical professionals and for self administering. Particularly, in its various embodiments and implementations, the invention provides for a proper supported positioning of the device relative to the cavity, a safe and effective range of discharge velocities of the lavage fluid, a clean and reliable evacuating of the waste fluid directly from the cavity, and the visual indication of safe and usable temperatures of the lavage fluid. Furthermore, the present invention facilitates preventing potential contaminations, saves time of the medical professionals by eliminating unnecessary preparation and clean-up procedures, and may save time and expenses for the prospective patients. Moreover, in its various embodiments and implementations, the invention provides for ecologically friendlier use of resources.

In general, in one aspect, a body cavity irrigation device comprising: a pump with an inlet and an outlet, a container for lavage fluid fastened removably to said pump, an applicator having an insertion tip, and divided longitudinally into an injection chamber with a first fitting and a drain chamber with a second fitting, and a first tube connecting said outlet to the first fitting wherein the first tube comprises at least one malleable element embedded longitudinally into an elastic wall, said inlet communicates with the lavage fluid within the container, and the drain chamber is disposed predominantly below the injection chamber and has at least one vent beyond the insertion tip. Various embodiments and implementations of this aspect of the invention include the following features:

The insertion tip is sized to seal against the lavage fluid by conforming to entrance walls of said body cavity and at least part of an external surface of the insertion tip is formed by a compliant element. The applicator further comprises a flow regulating check valve for regulating a velocity of the lavage fluid exiting the insertion tip, said flow regulating check valve at least partially inserted into the first fitting. The flow regulating check valve opens a flow orifice at a first predetermined pressure differential of the lavage fluid across said flow regulating check valve and, after reaching a second predetermined pressure differential of the lavage fluid across the flow regulating check valve, decreases an area of the flow orifice generally proportionally to an increase of a pressure differential of the lavage fluid across the flow regulating check valve. At least one temperature sensor capable of visual representation of temperatures in a range useful for functioning of the lavage fluid wherein said temperature sensor comprises a color changing film applied to a wall of the container. A second tube is attached to the second fitting wherein said second tube is flexible and may connect the second fitting to a waste container and/or to a vacuum source for evacuating the lavage fluid drained from the body cavity.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The following detailed description is not to be taken in a limiting sense, but is made merely for the purpose of illustrating the general principles of the invention, since the scope of the invention is best defined by the appended claims.

Figure 1:
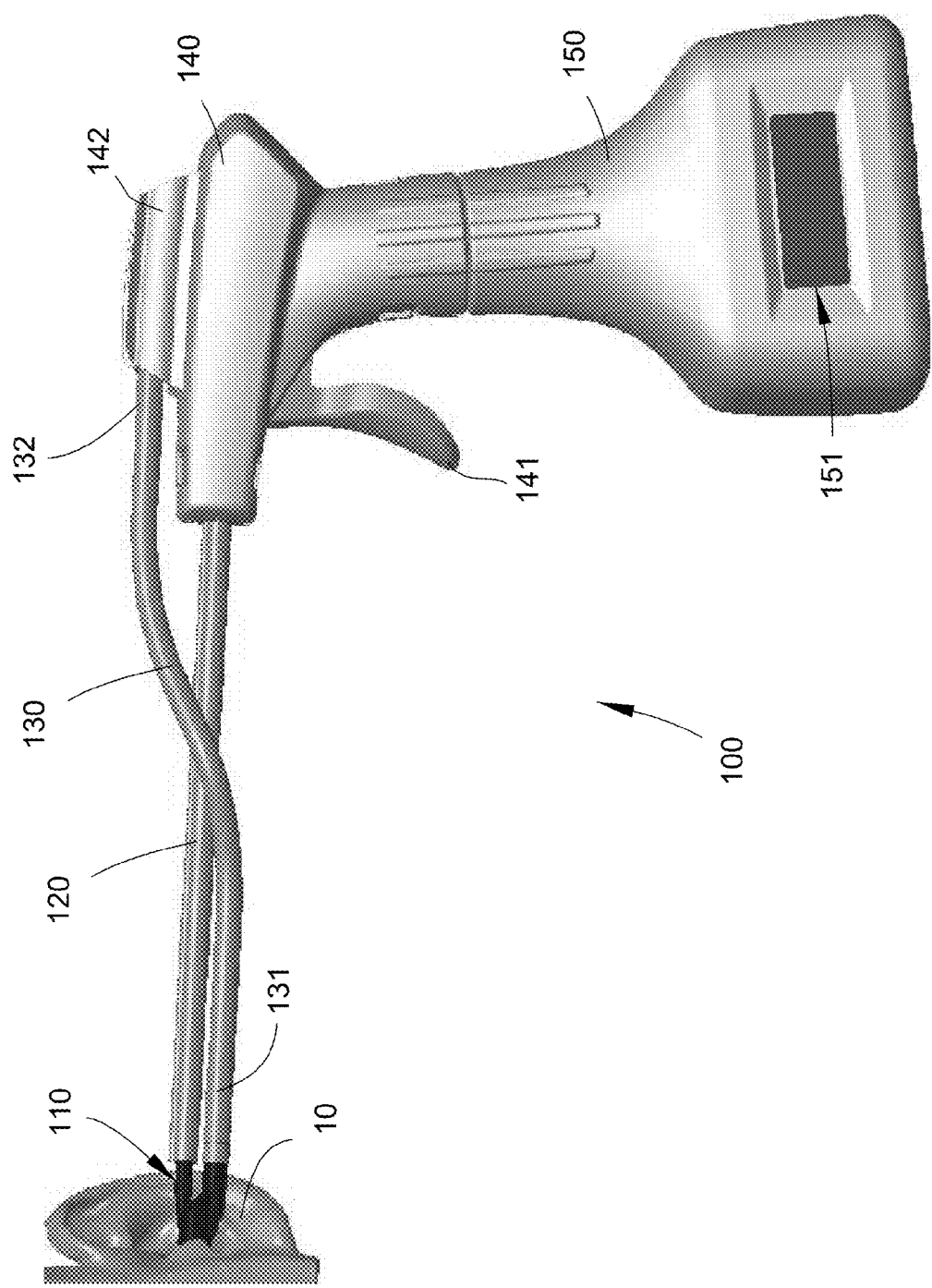
FIG. 1 depicts a shaded perspective view of the device in relation to a treated ear according to present invention.
Figure 2:
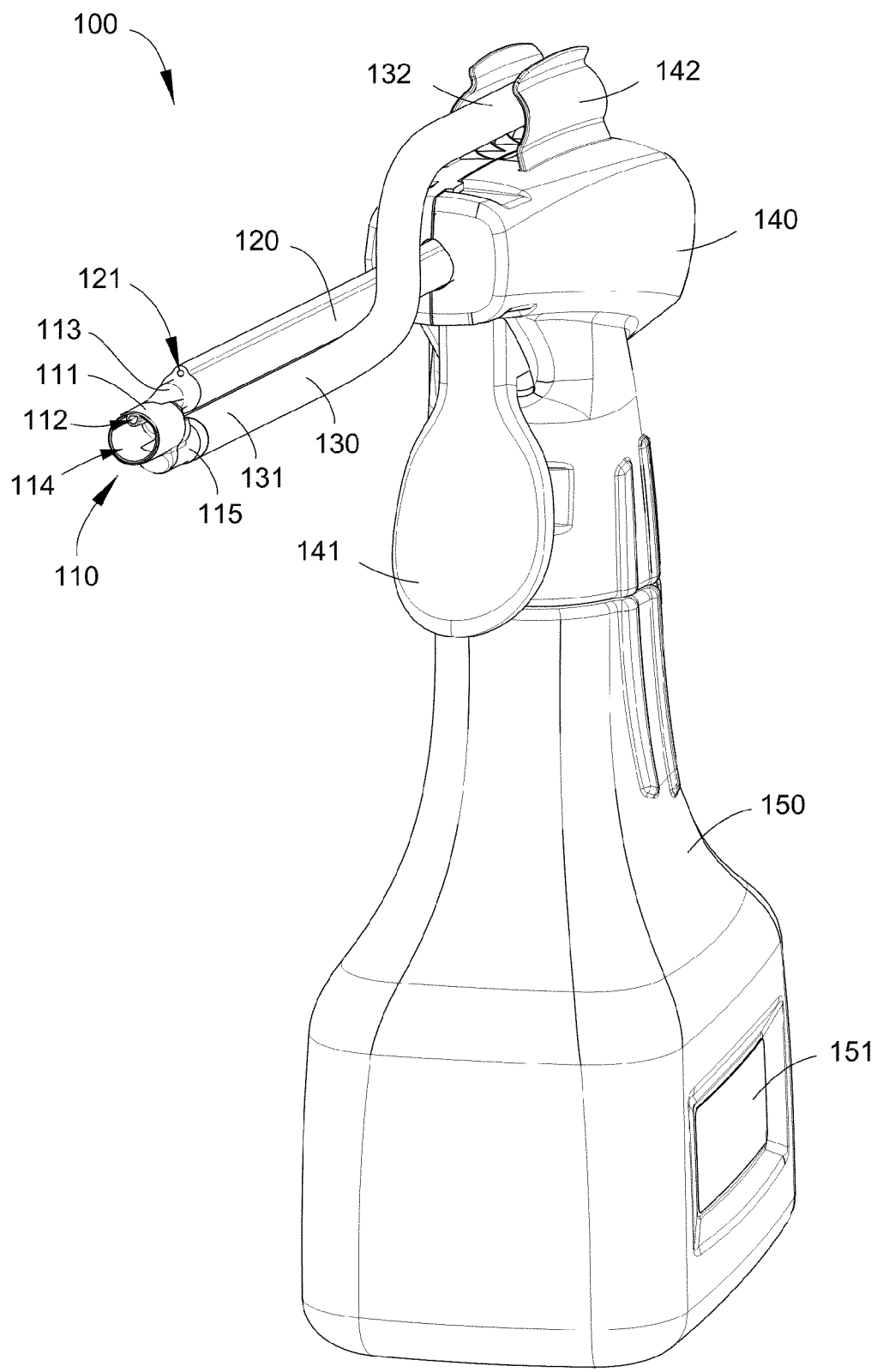
FIG. 2 depicts a perspective view of the device according to present invention.

In its various embodiments, the present invention focuses on a device for irrigating a body cavity, particularly an external ear canal. Referring to FIGS. 1-2, in one embodiment, an applicator 110 of the device 100 may be inserted into the external ear canal of ear 10. A feeding tube 120 connects the applicator 110 to a pump 140, which has a trigger 141 biased outward and a holder 142. A drain tube 130 connects to the applicator 110 with a first end 131 and to a vacuum line (not shown) with a second end 132 wherein the holder 142 may support a junction of the second end 132 and the vacuum line. A container 150 with a temperature indicator 151 may be fastened to the pump 140.

For the purpose of current disclosure, term 'pump' means a component comprising an inlet, an outlet, a mechanism that may move a liquid from the inlet to the outlet by creating the vacuum at the inlet and the pressure at the outlet, and, optionally, parts for attaching the feeding tube 120, the trigger 141, and the container 150. Furthermore, it should be understood, the inlet communicates with the container 150 in such a way that about an entire content of the container 150 may be removed by the pump. Moreover, means for attaching the feeding tube 120, the trigger 141, and the container 150 as well as various pumps suitable in the context of the current invention are well known in the art.

Referring to the drawing shown in FIG. 2, in one embodiment, the present invention contemplates the applicator 110 comprising an insertion tip 111 and divided longitudinally into an injection chamber 112 terminating as a feeding fitting 113 and a drain chamber 114 terminating as a drain fitting 115. The feeding tube 120 comprising a malleable metal wire 121 is placed over the feeding fitting 113 and the first end 131 is placed over the drain fitting 115.

In another embodiment the present invention, the second end 132 of the drain tube 130 may be terminated in a waste bag instead of the vacuum line. In yet other embodiments of the present invention, the second end 132 of the drain tube 130 may be attachable to a waste container, which may be separate from, attachable to, or a part of the container 150. Furthermore, the drain tube 130 may comprise a filter for collecting and analyzing solid particles removed from the ear 10.

Figure 3A:
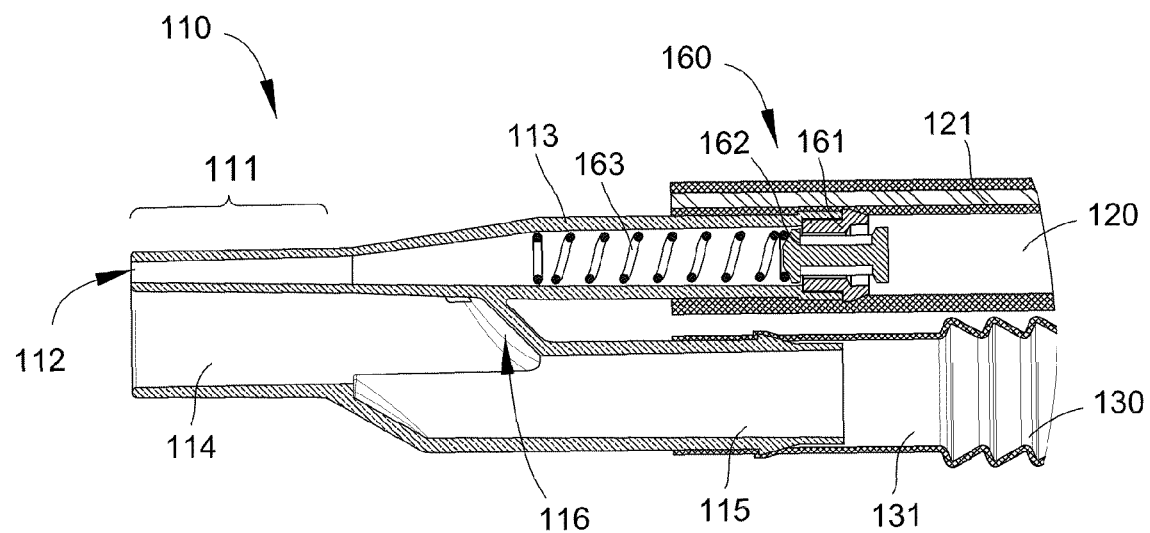
FIG. 3A depicts a detail section view of an embodiment of the device according to present invention.
Figure 3B:
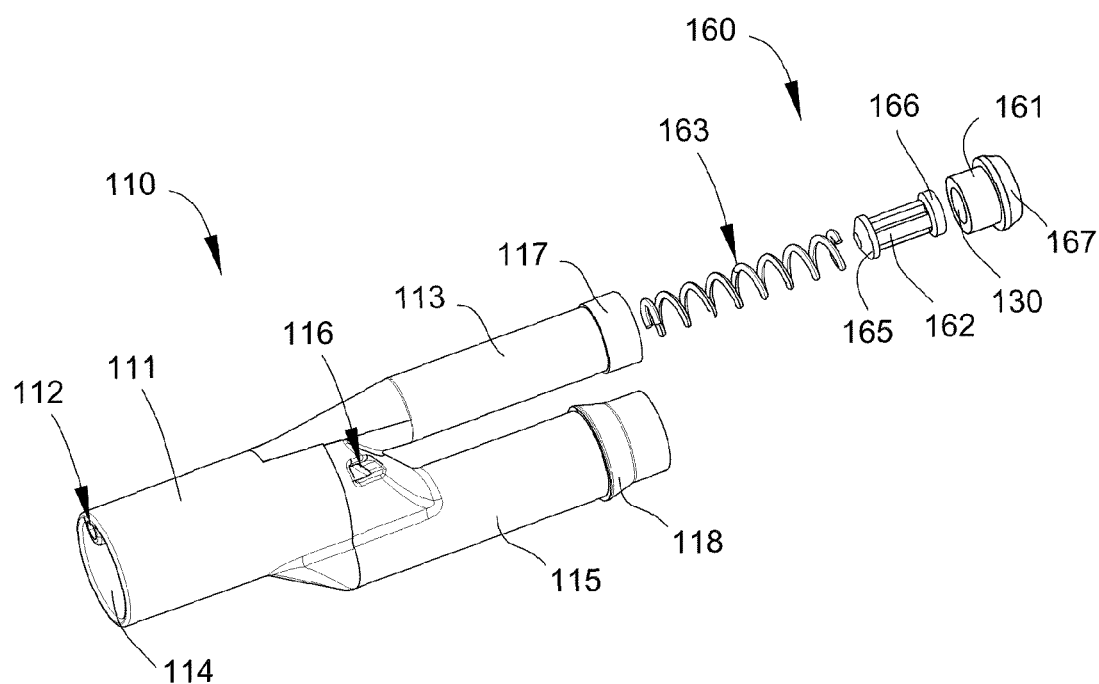
FIG. 3B depicts an exploded view of the applicator shown in FIG. 3A.

Referring to FIGS. 3A-3B, in one of embodiments of the present invention, the applicator 110 includes a valve 160 placed into the feeding fitting 113. The valve 160 comprises a seat 161, a plunger 162 with an underpressure stopper 165 and an overpressure limiter 166, and a spring 163. The seat 161 may be made of elastic material, for example polyurethane, to allow insertion through of the overpressure limiter 166 and has a chamfer 167 for assisting in pulling of the feeding tube 120 over the feeding fitting 113. Alternatively, the seat 161 may be made from rigid material with a median split to allow assembling of the valve 160. Relative to other surfaces of the feeding fitting 113, an end 117 has increased both an outer diameter for holding the feeding tube 120 and an inner diameter for accommodating the seat 161. Vents 116 may be placed through walls of the drain chamber 114 in an area of transitioning it into the drain fitting 115 beyond the insertion tip 111, outer surface of which may be essentially a cylinder sized to fit against an inner surface of the external canal of the ear 10. At least a part of the outer surface of the tip 111 may be formed with an additional layer of compliant material, for example, closed cell plastic foam or a compliant element (not shown) known in the art. The drain fitting 115 comprises a barb 118 for holding the first end 131 of the drain tube 130, which may be corrugated for combining a lengthwise flexibility with sectional stability.

Figure 4A:
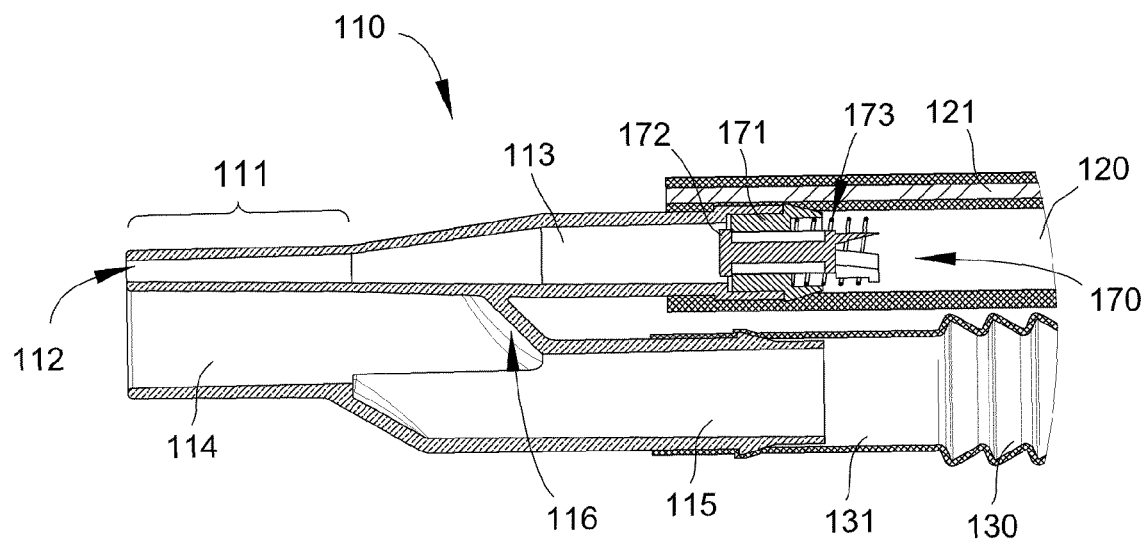
FIG. 4A depicts a detail section view of another embodiment of the device according to present invention.
Figure 4B:
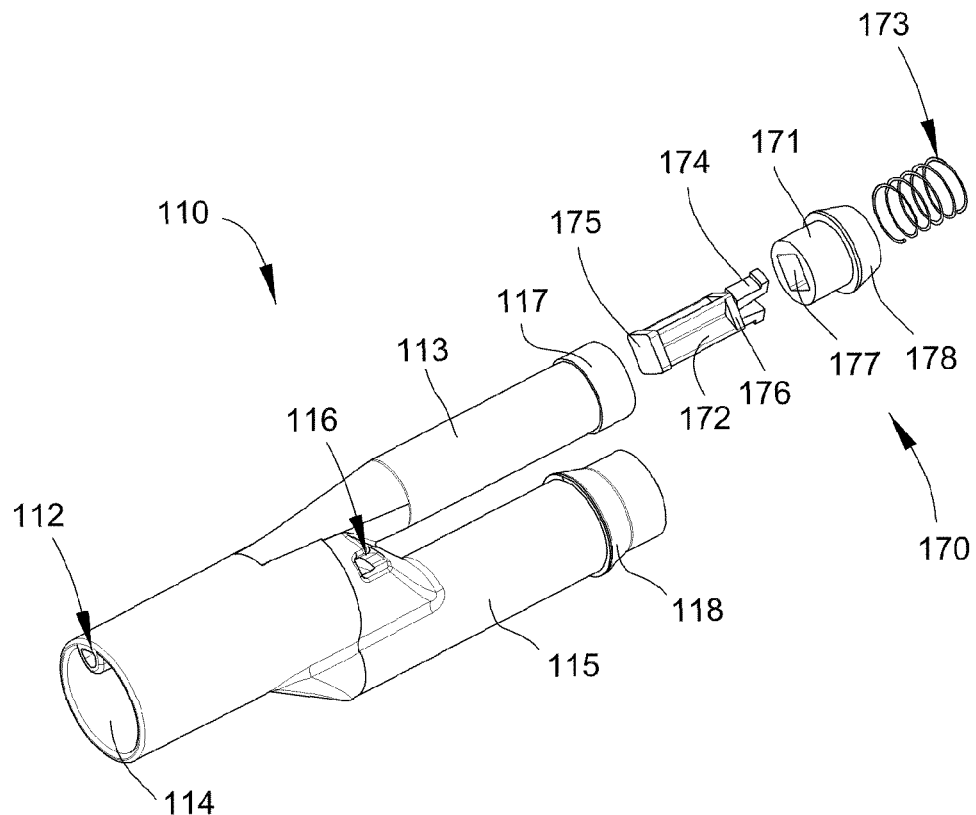
FIG. 4B depicts an exploded view of the applicator shown in FIG. 4A.

Referring to FIGS. 4A-4B, in another embodiment of the present invention, the applicator 110 includes a valve 170 placed into the feeding fitting 113. The valve 170 comprises a seat 171, a plunger 172 with an underpressure stopper 175, an overpressure limiter 176, and latches 174 and a spring 173. The seat 171 with an axial square hole 177 has a chamfer 178 for assisting in pulling of the feeding tube 120 over the feeding fitting 113. The overpressure limiter 176 may fit in the square hole 177 and the latches 174 may be bendable to allow assembling of the valve 170. The plunger 172 may have a changing section area along its length providing for changing of the flow resistance depending on position of the plunger 172 in the seat 171. The increased outer diameter of the end 117 may assist in holding the feeding tube 120 and the inner diameter may accommodate the seat 171.

One exemplary embodiment of the present invention functions as follows. Prior to using the device 100 (FIGS. 1-2), the container 150 may be filled with lavage fluid of appropriate temperature and fastened to the pump 140. Alternatively, the container 150 filled with the lavage fluid may be heated up to the appropriate temperature. The temperature indicator 151 may change its color indicating the appropriate temperature. Pressing the trigger 141 activates the pump 140, which displaces an amount of the lavage fluid from the container 150 through the feeding tube 120 and the injection chamber 112 of the applicator 110 into the ear 10. After irrigating the ear 10, the lavage fluid becomes a waste that drained through the drain chamber 114 of the applicator 110 and the drain tube 130 into the waste container. The wire 121 may allow bending the feeding tube 120 for greater convenience during the procedure and, at same time, supports the applicator 110 maintaining a seal between the external ear canal of the ear 10 and the insertion tip 111 (FIGS. 3A, 4A) of the applicator 110.

Referring to FIGS. 3A-3B, in a particular embodiment of the present invention, the lavage fluid transfers pressure from the outlet of the pump 140 to the valve 160 that pushes the plunger 162 against the spring 163. Parameters of the spring 163 together with geometry of the valve 160 and the injection chamber 112 define an injection pressure of the lavage fluid. When the pressure exceeds a defined minimum, the plunger 162 moves and allows the lavage fluid to flow around the stopper 165. With the pressure increasing, the plunger 162 would move further that, at some point, would restrict the flow of the lavage fluid between the seat 161 and the overpressure limiter 165. Consequently, due to increased resistance in the valve 160, energy of the lavage fluid discharged from the injection chamber 112 would not exceed certain safe level. The valve 160 would remain open as long as pressure losses across the valve 160 and in the injection chamber 112 together are equal to the pressure upstream of the valve 160. At extreme rise of the pressure, the overpressure limiter 166 may be pressed against the seat 161 stopping the flow entirely.

The waste fluid enters the drain chamber 114 and flows along the drain tube 130. If the drain tube 130 connects to a vacuum source, the vents 116 prevent premature evacuation of the lavage fluid by allowing air from outside to enter the drain tube 130. In case the drain tube 130 terminates into a closed container or bag, the vents 116 break what otherwise would be a closed loop preventing a pressure buildup in the cavity.

Referring to FIGS. 4A-4B, in another embodiment of the present invention, the valve 170 may be applicable to low pressure pumps. Due to square shape of the underpressure stopper 175, the flow of the lavage fluid around the stopper 175 may be less restricted. Furthermore, due to the overpressure limiter 176 fitting into the square hole 177, the flow would not be stopped completely but, instead, would depend on a clearance between the limiter 176 and the hole 177.

Consequently, the present invention provides the improved body cavity irrigation device that is safe, easy and convenient to use by medical professionals and for self administering. Particularly, the invention provides for a fully recyclable device either disposable entirely or having the container 150 with the temperature indicator 151 reusable. Consequently, the present invention may prevent contaminations, saves time of the medical professionals by eliminating unnecessary preparation and clean-up procedures, and may enable self serving for the prospective patients.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Accordingly, as indicated above, the foregoing embodiments of the invention are examples and can be varied in many ways. Such present or future variations are not to be regarded as a departure from the spirit and scope of the invention, and all such modifications as would be apparent to one skilled in the art are intended to be included within the scope of the following claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the term "about" refers to a ±10% variation from the nominal value. It is to be understood that such a variation is always included in any given value provided herein, whether or not it is specifically referred to.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively

We claim:

1. A body cavity irrigation device comprising:
   a manual trigger activated pump with an outlet for supplying lavage fluid,
   an applicator having an insertion tip for at least partially inserting of said applicator into an opening of said body cavity, said applicator divided longitudinally into
   an injection chamber with a first fitting and
   a drain chamber with a second fitting;
   a first tube connecting said outlet to said first fitting; and
   a flow regulating check valve for regulating energy of said lavage fluid exiting said insertion tip;
   wherein said flow regulating check valve at least partially disposed inside of said first tube, said first tube comprises at least one malleable clement embedded longitudinally into an elastic wall, said malleable clement configured to assume and maintain a predetermined shape, and said drain chamber is disposed predominantly below said injection chamber and has at least one vent between said second fitting and said insertion tip.

2. The device of claim 1, wherein said flow regulating check valve is at least partially inserted into said first fitting.

* * * * *